United States Patent [19]

Kopp

[11] Patent Number: 4,776,837
[45] Date of Patent: Oct. 11, 1988

[54] SINGLE LUMEN CATHETER FLUID TREATMENT

[76] Inventor: Klaus F. Kopp, Aschlkofener Str. 4, D-8017 Ebersberg, Fed. Rep. of Germany

[21] Appl. No.: 33,858

[22] Filed: Apr. 6, 1987

Related U.S. Application Data

[63] Continuation of Ser. No. 847,135, Apr. 1, 1986, abandoned, which is a continuation of Ser. No. 506,886, Jun. 21, 1983, abandoned.

[51] Int. Cl.⁴ .............................................. A61M 1/03
[52] U.S. Cl. ........................................ 604/4; 604/110; 128/DIG. 13
[58] Field of Search ........................................ 604/4–7, 604/28–31, 34, 51, 52, 67, 118, 131, 190, 191, 245, 246; 128/DIG. 3, DIG. 12, DIG. 13, DIG. 22

[56] References Cited

U.S. PATENT DOCUMENTS

| | | | |
|---|---|---|---|
| 3,017,885 | 1/1962 | Robicsek | 604/4 |
| 3,756,234 | 9/1973 | Kopp | 604/5 |
| 3,830,234 | 8/1974 | Kopp | 604/30 |
| 3,881,483 | 5/1975 | Sausse | 604/118 |
| 3,902,490 | 9/1975 | Jacobsen et al. | 604/5 |
| 3,908,653 | 9/1975 | Kettering | 604/5 |
| 4,353,368 | 10/1982 | Slovák | 604/4 |
| 4,385,630 | 5/1983 | Gilcher | 604/31 |
| 4,464,164 | 8/1984 | Troutner et al. | 604/5 |
| 4,526,568 | 7/1985 | Clemens et al. | 604/4 |

OTHER PUBLICATIONS

IBM Technical Disclosure Bulletin, vol. 19, No. 3, Aug. 1976.

Primary Examiner—Stephen C. Pellegrino
Attorney, Agent, or Firm—Browdy and Neimark

[57] ABSTRACT

The invention concerns a novel procedure and apparatus for controlling opening and closing of venous and arterial lines in single lumen catheter fluid treatment procedures. Different types of apparatus useful for different types of fluid treatment procedures, in particular hemodialysis, hemofiltration, and plasmapheresis procedures, are disclosed.

8 Claims, 3 Drawing Sheets

SINGLE LUMEN CATHETER FLUID TREATMENT

This application is a continuation of application Ser. No. 847,135 filed Apr. 1, 1986, now abandoned which is a continuation of application Ser. No. 506,886 filed June 21, 1983 now abandoned.

This invention relates to single lumen catheter fluid treatment, and more particularly to a method and apparatus for controlling opening and closing of venous and arterial lines leading to and from said single lumen catheter.

BACKGROUND OF THE INVENTION

A variety of procedures and apparatuses related to single lumen catheter fluid treatment, more particularly blood treatment, have developed since the time of my U.S. Pat. No. 3,756,234, now U.S. Pat. No. Re 29,346. The most successful procedures or apparatuses employ the concept of controlling at least one of opening or closing of the venous or arterial line in response to a high or low pressure value which develops in a closed extracorporeal blood circuit, comprising the arterial line leading from the single lumen catheter, the hemodialyser, hemofilter, hemodiafilter, plasmapheresis device, or ascites device, and the venous line, which venous line normally includes a venous line reservoir or drip chamber, leading back to the single lumen catheter. Most popular are procedures involving opening of the venous line with substantially simultaneous closing of the arterial line in response to a preset higher pressure value which develops in the venous line. These procedures sometimes also involve closing of the venous line with substantially simultaneous opening of the artierial line in response to a preset lower pressure value which develops in the venous line. Generally, the pressure value in the venous line is sensed by sensing pressure in a gaseous cushion above the level of fluid, usually purified or treated blood, in the venous line reservoir. Also known are devices in which closing of the venous line with substantially simultaneous opening of the arterial line is in response to a predetermined or adjustable time increment. Similarly, devices in which closing of the arterial line with subtantially simultaneous opening of the venous line is in response to a predetermined or adjustable time increment are known, which devices may either include means for closing of the venous line with substantially simultaneous opening of the arterial line in response to a preset lower pressure value which develops in the venous line, or may include means for closing of the venous line with substantially simultaneous opening of the arterial line in response to a predetermined or adjustable time increment. The latter type of device, i.e. one in which closing of both the arterial and venous lines is in response to predetermined or adjustable time increments are not contemplated by my U.S. Pat. No. Re 29,346 and indeed have been avoided in further research for the reason that control of single lumen catheter fluid treatment procedures exclusively by timer mechanisms excludes achieving what is considered to be an extremely important advantage. Devices including means for closing of the arterial or venous lines in response to a pressure value which develops in the extracorporeal blood circuit are controlled dependently of a particular condition or status within the extracorporeal blood circuit. In other words, systems including means for controlling closing of the arterial and/or venous lines in response to a pressure value developed in the extracorporeal blood circuit are essentially self-regulating. With the above considerations in mind, and in particular bearing in mind the concept of achieving a self-regulating system, it has now been found that a particular combination of means for controlling closing of venous and arterial lines in a single lumen catheter assembly can achieve substantially improved self-regulation as compared to systems employed in the past. More particularly, it has been observed that self-regulation in a single lumen catheter assembly is not complete if there is not also provided means for controlling closure of the venous line dependently of conditions in the arterial line. This consideration, coupled with the procedure of controlling closure of the arterial line dependently of conditions in the venous line, already known in part from devices such as discussed above, has led to a new and greatly improved method and apparatus useful for controlling the closing of an arterial line with substantially simultaneous opening of a venous line and the closing of said venous line with substantially simultaneous opening of said arterial line, which method and apparatus is the subject of the present invention. An assembly of fluid lines specially adapted for the method and apparatus is also provided by the present invention.

The present invention furthermore includes the consideration that there is little point in closing the venous line whilst there is an adequate quantity of untreated fluid upstream of the fluid treatment device. Similarly, or conversely, there is little point in closing the arterial line with substantially simultaneous opening of the venous line before there is an adequate quantity of treated fluid downstream of the fluid treatment device. It is of importance to bear in mind that time should be optimally employed in single lumen catheter fluid treatment procedures since if treatment time with a single lumen catheter exceeds treatment time with double lumen or dual needle treatment procedures too significantly, the now well-known advantages of some single lumen catheter fluid treatment procedures could be outweighed by such increased fluid treatment time.

SUMMARY OF INVENTION

The method of the present invention comprises the steps of providing an arterial line reservoir upstream of the fluid treatment device for receiving untreated fluid from the fluid source, providing an arterial line opening and closing means upstream of the arterial line reservoir, providing a venous line reservoir downstream of the fluid treatment device for receiving treated fluid from the fluid treatment device, providing a venous line opening and closing means downstream of the venous line reservoir, withdrawing untreated fluid from said fluid source into said arterial line reservoir, passing such untreated fluid from said arterial line reservoir through the fluid treatment device and into the venous line reservoir, closing the arterial line and substantially simultaneously opening the venous line in response to a higher limit quantity of treated fluid available in the venous line reservoir whereby treated fluid is returned to said fluid source, and closing the venous line and substantially simultaneously opening the arterial line in response to a lower limit quantity of untreated fluid available in the arterial line reservoir. The arterial and venous line closing and opening means may be achieved in now conventional fashion, such as with solenoid-operated clamps or stopping and starting of fluid pumps conveniently peristaltic roller pumps. Generally, however, in the present invention, untreated fluid would be continuously passed from said arterial line reservoir and through the fluid treatment device so that treated fluid is continuously collected in the venous line reservoir. Thus, clamp means for controlling opening and closing of the arterial line would in general be provided upstream of an arterial line fluid pump and upstream of the arterial line reservoir. Similarly, in general, clamp means for opening and closing the venous line would be provided downstream of the venous line reservoir.

In a simpler embodiment of the present invention only one pump means is provided for the purpose of passing untreated fluid from the arterial line reservoir and through the fluid treatment device so that treated fluid is collected in the venous line reservoir. In this embodiment, pressure would fluctuate not only in the venous line reservoir but also in the fluid treatment device. This may not always be desirable, as in certain hemodialysis procedures in which so-called high-flux membrane fluid treatment devices are employed or in certain hemofiltration, hemodiafiltration, or plasmapheresis operations. In such operations, it would in general be of advantage if the fluid pressure in the fluid treatment device were to remain substantially constant.

As is described in greater detail below, with reference to the accompanying drawings, a measure of protection of pressure values can be achieved by increasing the volumetric proportion of a gaseous cushion in the venous line reservoir in relation to liquid volume therein. However, a dual pump system, involving the above considerations and including a first fluid pump upstream of the fluid treatment device and a second fluid pump downstream of the fluid treatment device and means for controlling pump speeds dependently of pressure between the two pumps, provides more reliable control of fluid pressure between the pumps and in the fluid treatment device.

The method and devices discussed above, and various further aspects of or related to the present invention are described below with reference to the accompanying drawings. The description with reference to the accompanying drawings also describes a single lumen catheter procedure and apparatus in accordance with the invention applied to a novel plasmapheresis procedure. This plasmapheresis procedure, however, could also be performed employing techniques other than a single lumen catheter technique. The plasmapheresis procedure, and apparatus in accordance with the invention including a single lumen catheter approach is described below with reference to the accompanying drawings.

BRIEF DESCRIPTION OF DRAWINGS

The invention will now be described with reference to the accompanying drawings showing exemplary constructions of apparatuses in accordance with the invention.

In the drawings.

DETAILED DESCRIPTION OF EMBODIMENTS OF DRAWINGS

Figure 1:
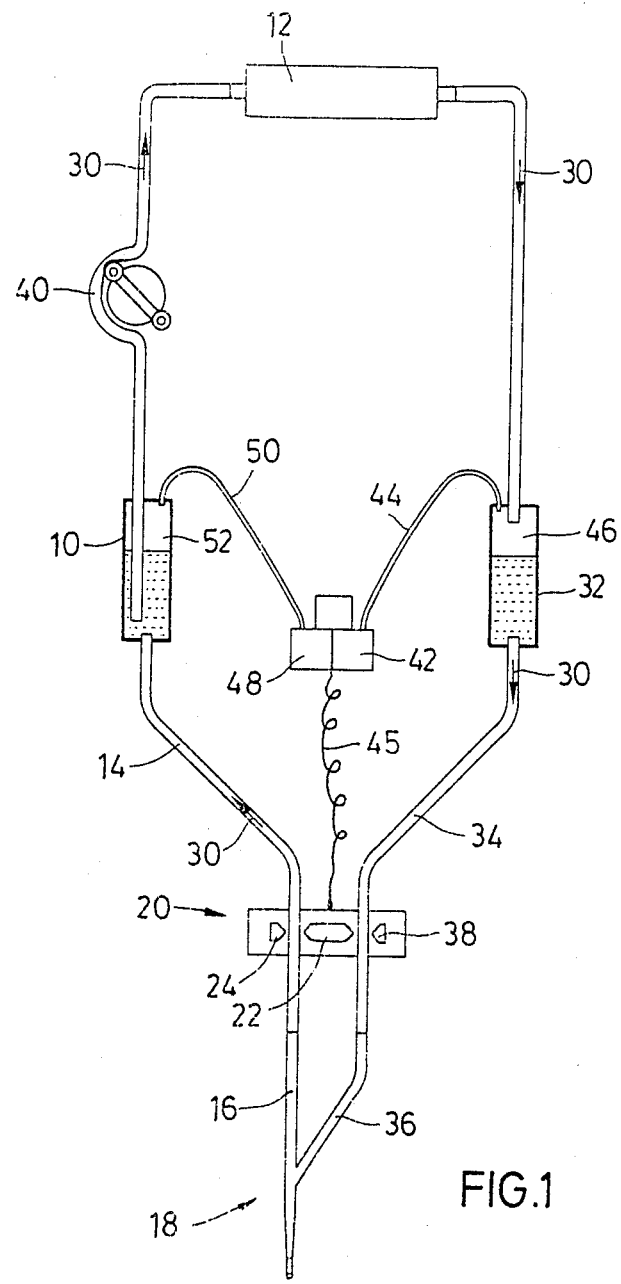
FIG. 1 shows a schematic representation of an apparatus and fluid lines operable with a single fluid pump.

Referring to FIG. 1, reference numeral 10 refers to an arterial line reservoir, which is located upstream of a fluid treatment device 12. The fluid treatment device employed in this apparatus would in general be a conventional hemodialyser, which could also be of high flux nature if adequate means for controlling ultrafiltration is available. An arterial line 14 leads from a first arm 16 of a single lumen catheter assembly, referred to generally by reference numeral 18, and into the arterial line reservoir 10.

Figure 2:
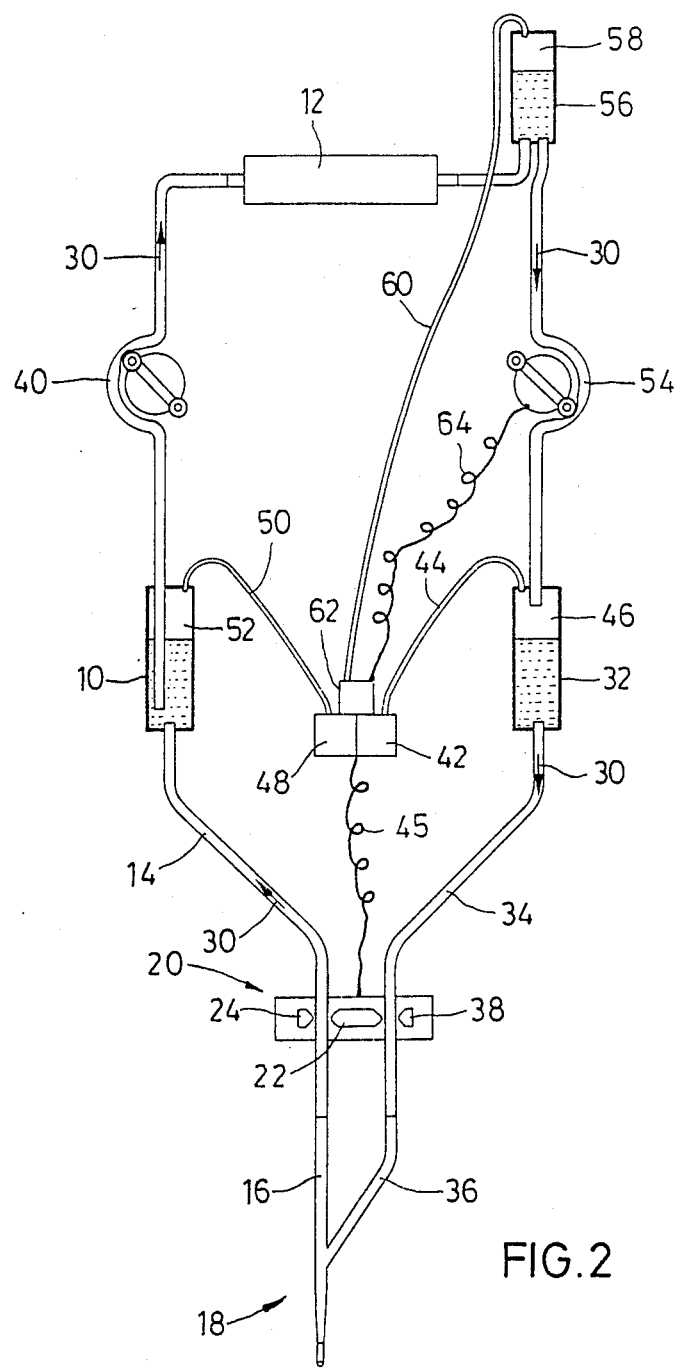
FIG. 2 shows a schematic representation of an apparatus and fluid lines operable with two fluid pumps.
Figure 3:
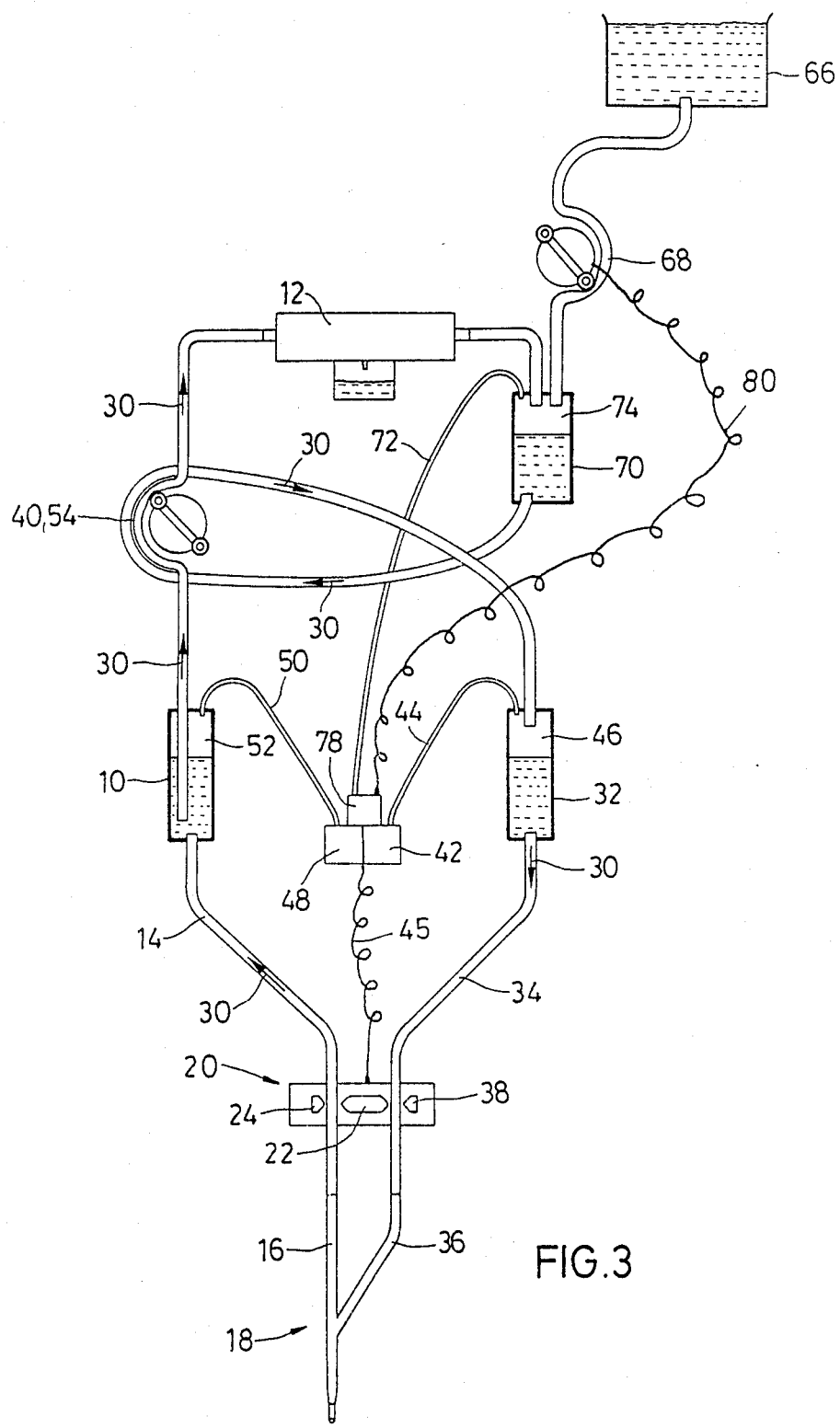
FIG. 3 shows a schematic representation of an apparatus and fluid lines operable with a so-called double-head fluid pump and a further pump for introducing a substitution fluid.

Arterial line opening and closing means and venous line opening and closing means, referred to generally by reference numeral 20, are in the schematic drawing of FIG. 1 and also in FIGS. 2 and 3, shown by way of example to be a combined or single unit. Thus, the arterial line opening and closing means constitutes a central member 22 displaceable to the left and right in the plane of the drawings between a first extreme position to the left in which the arterial line 14 is closed or occluded between the central member 22 and a first abutment element 24 and an extreme position to the right in which the arterial line is open. Closing and opening of the arterial line takes place upstream of the arterial line reservoir 10, arrow-heads 30 depicting fluid flow direction.

Reference numeral 32 refers to a venous line reservoir downstream of the fluid treatment device 12. A venous line 34 leads from the venous line reservoir 32 to a second arm 36 of the single lumen catheter assembly 18. As already mentioned, venous line opening and closing means is comprised in the combined or single unit referred to generally by reference numeral 20. The venous line opening and closing means constitutes the central member 22 displaceable to the right and left in the plane of the drawings between an extreme position to the right in which the venous line 34 is closed or occluded between the central member 22 and a second abutment element 38 and an extreme position to the left in which the venous line is open. Closing and opening of the venous line 34 takes place downstream of the venous line reservoir 32.

The apparatus of FIG. 1 comprises a single fluid pump 40, conveniently of the roller pump type, for passing untreated fluid from the arterial line reservoir 10, through the fluid treatment device 12 and into the venous line reservoir 32.

High limit sensor means for sensing a higher limit quantity of treated fluid available in the venous line reservoir 32, comprises a high pressure value sensor 42 adapted to transmit a first signal via electrically conductive wire 45 to the arterial and venous line opening and closing unit 20 when a predetermined or preset high pressure value is reached in the pressure sensor 42. This high pressure value is transmitted to the oressure sensor 42 via pressure transmitting conduit 44 which transmits the pressure which develops in a gaseous cushion 46 in the venous line reservoir 32. When the predetermined or preset high pressure value is reached in the venous line reservoir 32 and accordingly also in the pressure sensor 42, the first signal transmitted via electrically conductive wire 45 results in the displaceable member 22 being displaced to the left extreme in which the arterial line 14 is closed or occluded between the displaceable member 22 and the first abutment element 24.

The fluid pump 40 then continues to pass untreated fluid from the arterial line reservoir 10 through the fluid treatment device 12 and into the venous line reservoir 32 until a lower limit quantity of untreated fluid is available in the arterial line reservoir 10. Low limit sensor means for sensing a lower limit quantity of untreated fluid in the arterial line reservoir 10, comprises a low pressure value sensor 48 adapted to transmit a second signal, conveniently via the same electrically conductive wire 45, to the arterial and venous line opening and closing unit 20 when a predetermined or preset low pressure value is reached in the pressure sensor 48. This low pressure value is transmitted to the pressure sensor 48 via pressure transmitting conduit 50 which transmits the pressure which develops in a gaseous cushion 52 in the arterial line reservoir 10. When the predetermined or preset low pressure value is reached in the arterial line reservoir and accordingly also in the pressure sensor 48, the second signal transmitted results in the displaceable member 22 being displaced to the right extreme in which the venous line 34 is closed or occluded between the displaceable member 22 and the second abutment element 38.

It will be appreciated from the above description that closing of the arterial line 14 will lead to substantially simultaneous opening of the venous line 34 during operation of the apparatus. Similarly, closing of the venous line 34 will lead to substantially simultaneous opening of the arterial line 14.

Mentioned above is a fluctuating pressure in the venous line reservoir 32. It is in most situations desirable that pressure in the venous line reservoir 32 not fall very much below the predetermined or preset high pressure limit, since high pressure (i.e. higher than fluid pressure at the fluid source) in this construction of the invention is the driving force leading to return of fluid to the fluid source through the venous line 34 and catheter assembly 18 whilst the venous line is open. The volume of treated fluid returned to the fluid source per unit time is the important factor, which is of course greatest when the pressure value is at or near the high pressure limit. Furthermore a degree of stability of pressure in the venous line reservoir 32 and accordingly also in the fluid treatment device can be of advantage in achieving an improved control of ultrafiltration rate, as for example in constructions in which ultrafiltration rate is controlled by transmembrane pressure. In order to better preserve the high pressure value, it has been found that this can be achieved by increasing the volumetric proportion of the air cushion 46 in the venous line reservoir 32 as related to the volume of liquid therein. Thus, if the total volume of venous line reservoir 32 is increased as compared to standard constructions (in which the volume of liquid in the reservoir occupies up to about three-quarters of the total volume of the reservoir) so that the volume of liquid in the reservoir occupies say only one third or less of the total volume, the high pressure value in reservoir is better preserved and does not fall below the high pressure value to the same extent. Similarly, in the construction of FIG. I of the drawings, it is desirable to better preserve the low pressure value in the arterial line reservoir 10, since the low pressure (in conjunction with pressure at the fluid source) is the driving force leading to withdrawal of fluid from the fluid source. Improved preservation of the low pressure value in the arterial line reservoir 10 can be achieved by increasing the volumetric proportion of the air cushion 52 as related to the volume of liquid therein, once again by suitably proportioning the volume of the arterial line reservoir.

Mentioned above in relation to FIG. I of the drawings is that it may be desirable in certain fluid treatment procedures to achieve a substantially constant pressure of fluid in the fluid treatment device 12. In the construction of FIG. I, it is necessary that a certain fluctuation of pressure take place in the venous line reservoir 32 and accordingly also in the fluid treatment device 12 in order that pressure can develop to the high level value leading to closing of the arterial line. This pressure fluctuation may not be desirable in certain fluid treatment procedures and may for example lead to inadequate control over volume of fluid passing from the fluid being treated across membrane material comprised in the fluid treatment device 12, as in hemodialysis employing so-called high-flux membrane dialysis, hemodiafiltration, hemofiltration or plasmapheresis procedures.

Accordingly, it can be necessary to isolate pressures which develop in the venous line reservoir 32 from fluid passing through the fluid treatment device 12. This is conveniently achieved by providing a second fluid pump downstream of the fluid treatment device 12 and upstream of the venous line reservoir 32. Such a conctruction is illustrated in FIG. 2 of the drawings, in which integers of FIG. I which are common to FIG. 2 are referred to by the same reference numerals.

In FIG. 2 of the drawings, there is no need to again describe functioning of the arterial line chamber 10, venous line chamber 32, high and low pressure values and operation of the arterial and venous line opening and closing means 20, which function essentially in the same fashion as described above in relation to FIG. I. A second fluid pump 54 is, in FIG. 2 provided downstream of the fluid treatment device 12 and upstream of the venous line reservoir 32. Fluid pressure between the pump 40 in the arterial line 14 and the second pump 54, i.e. including the fluid treatment device 12, is independent of pressure values which develop in the venous line reservoir 32, unlike the construction shown in FIG. I. In both the constructions of FIG. I and FIG. 2, the pump 40 isolates the pressure of fluid downstream of the pump 40 from pressure values which develop in the arterial line reservoir 10.

The pumps 40 and 54 in FIG. 2 may operate in a variety of fashions. However, as already mentioned in relation to FIG. I, the pump 40 in the arterial line 14 most preferably operates continuously, which is also the preference in the construction of FIG. 2. In the arrangement of FIG. 2, with a continuously operating pump 40, it has also been found to be preferable that the second pump 54 also operate continuously, which mode of operation is believed to be new in a dual pump single lumen catheter construction. Additionally and more particularly, a dual pump construction as shown in FIG. 2 in which relative pump speeds, i.e. the speed of pump 40 relative to the speed of pump 54, are controlled by fluid pressure between two continuously operating pumps is believed to be new, and is of high advantage over known dual pump systems presently available. Thus, a desired fluid pressure value may be selected, for example dependent on a desired ultrafiltration rate observed in a hemodialysis operation at a particular dialysis liquid pressure for a particular fluid treatment device 12. Conveniently, the speed of one or other of the fluid pumps 40 and 54 is operable at a constant speed which may be manually adjusted, and the speed of other fluid pump is variable in response to fluid pressure between the two pumps. In practice, it is preferable that the fluid pump 40 be the constant speed pump and the fluid pump 54 be the variable speed pump.

Fluid pressure between the two fluid pumps 40 and 54 may in the construction of FIG. 2 be sensed anywhere between the two pumps, i.e. upstream or downstream of the fluid treatment device 12, or if means therefor is available in the fluid treatment device itself. However, in practice, it has been found convenient to provide a pressure reservoir 56 downstream of the fluid treatment device 12, as shown in FIG. 2. The pressure reservoir 56 is shown in FIG. 2 to be essentially similar to the arterial line reservoir 10 and venous line reservoir 32, with a gaseous cushion 58, pressure transmitting conduit 60, and pressure sensor 62. However, it will be appreciated that another type of arrangement for sensing fluid pressure between the two fluid pumps 40 and 54 could function equally well or perhaps even better. For example, a pressure sensing arrangement including a flexible membrane (not shown) in contact on one side thereof with liquid between the two pumps, and a pressure transmitting liquid on the other side of the membrane would provide a greater impulse with pressure change than the illustrated arrangement including a compressible gas cushion. Thus, the control of the variable speed pump in response to pressure change between the two pumps could possibly be improved. In any event, in contrast to the preference for preserving pressure in the arterial line reservoir 10 and venous line reservoir 32, the pressure sensing arrangement should provide an impulse responding to the smallest of pressure changes to enable accurate control of the speed of the variable speed pump in response to pressure. The pressure sensor 62 in FIG. 2 is adjustable to any fixed pressure value, for example between 0 and example 220 mm Hg, and is adapted to control via electrically conductive wire 64 the amount of electrical current fed to the variable speed pump 54 so that this pump will be driven at that rate which will maintain the pressure value chosen in pressure sensor 62. For a given setting of the speed of the pump 40, for example a setting leading to about 200 ml/min of blood being delivered to the fluid treatment device 12, and a given pressure setting of the pressure sensor 62, the variable speed pump 54 will automatically adjust to that speed which maintains the pressure set in the pressure sensor 62. Improved management of ultrafiltration rate may be achieved by virtue of improved control over the pressure of liquid between the pumps 40 and 54. Presuming accurate control and adjustability of dialysis liquid pressure in a hemodialysis operation, transmembrane pressure can be controlled to achieve the desired ultrafiltration rate for a given hemodialyser (fluid treatment device 12).

The construction illustrated in FIG. 2 is of exceptional versatility and can for example find application in most types of extracorporeal blood treatment procedures such as in conventional hemodialysis, hemodiafiltration, hemofiltration and plasmapheresis. It has been found from practical experience with a so-called double-head blood pump in which the arterial line and venous line pumps are a single unit adapted to receive both a pump insert for pumping fluid from the arterial line reservoir to the fluid treatment device 12 and a pump insert for pumping fluid from the fluid treatment device 12 to the venous line reservoir, that such an arrangement is particularly suited for performing a novel type of plasmapheresis operation.

FIG. 3 of the drawings shows a construction comprising the abovementioned double-head blood pump. It has been found that a double-head blood pump as described above can in actual practice be employed to ensure that precisely the same volume of liquid as is withdrawn from a patient can be returned to the patient, practically independently of the nature of the fluid treatment device 12 connected between the two pumps. For example, it has been found that in a conventional hemodialysis treatment over a period of three to four hours, in which dialysis liquid in the fluid treatment device 12 is maintained at conventional negative pressures below atmospheric pressure, such as −100 mm Hg, no ultrafiltration and accordingly no patient weight loss takes place. This finding is associated with adequate or complete occlusion of both the arterial and venous line pump inserts in the double-head blood pump.

Referring now more particularly to FIG. 3 of the drawings, integers common to this Figure and FIGS. 1 and 2 are once again referred to by the same reference numerals. The construction of FIG. 3, however includes a double-head blood pump as above described and is conveniently referred to by double reference numeral 40-54 in view of the similarity (not identity) of function with the pumps 40 and 54 of FIG. 2.

Bearing in mind that the double-head blood pump 40-54 leads to precisely the same volume of liquid being withdrawn from the patient as is returned to the patient, any volume of liquid introduced into the fluid flow line comprising the fluid treatment device 12 (plasmapheresis device 12 in FIG. 3), i.e. downstream and upstream of the double-head blood pump, will lead to precisely the same volume of liquid being forced through membrane material comprised in the plasmppheresis device 12. Arrow-heads 30 once again depict fluid flow direction. Accordingly, if the volume of liquid introduced is monitored, the volume of liquid (plasma) forced through the membrane material is automatically also monitored. In FIG. 3, there is shown a container 66 for containing replacement or substitution fluid, a fluid pump 68 for introducing substitution fluid into a pressure chamber 70 provided downstream of the plasmapheresis device 12 and upstream of the double-head blood pump 40-54. A pressure-transmitting conduit 72 is provided for transmitting pressure in a gaseous cushion 74 in the pressure chamber 70 to a pressure sensor 78. The pressure sensor 78 is conveniently adjustable to any fixed pressure value, for example between 0 and 200 mm Hg. The fluid pump 68 may be a variable speed pump, variable to maintain the pressure value fixed in pressure sensor 78. An electrically conductive wire 80 leading from the pressure sensor 78 to the fluid pump 68 is shown for providing a pressure-dependent feed-back to the pump 68. However, it will be understood that the pump 68 may be a manually adjustable variable speed pump of a volumetric type adapted to introduce a desired volume of substitution fluid per unit time. In such an arrangement, the pressure sensor 78 and feed-back to the pump 68 would be a preferable feature, for example for ensuring that fluid pressure in the plasmapheresis device 12 does not exceed a maximum limit. In this latter arrangement, the pressure sensor 78 and the feed-back to the pump 68 would function to ensure that the pump speed of pump 68 is not manually set at a rate which for example exceeds the capacity of the plasmapheresis device 12 to separate plasma from whole blood at a safe maximum pressure value which can be set in pressure sensor 78.

The methods and apparatus in accordance with the present invention include considerations particularly related to simplicity of use and safety. Regarding simplicity of use, for example of the apparatus of FIG. 1, the high pressure sensor 42 may be fixed at a high pressure value of for example 250 mm Hg, and the low pressure sensor 48 may be fixed at a low pressure value of for example −120 mm Hg. Presuming standard blood tubing sets with a standard pump insert, even the speed of the pump 40 can be fixed to deliver about 200 ml/min of blood to the fluid treatment device 12. Other than standard priming operations, practically nothing is required of attending staff. It is however most preferable that the pump 40 be a variable speed pump which is conveniently manually adjustable so that this may be adjusted to the maximum stroke volume, i.e. so that maximum use is made of available blood flow, from the fistula or vein of a patient. Also, for the event that the speed of the pump is set to run too fast (leading to a pressure lower than the low pressure value) an alarm (not shown) condition will be reflected indicating insufficient availability of blood from the patient fistula or vein. It may therefore be necessary to lower the speed of the pump.

Similar to above, the apparatuses of FIGS. 2 and 3, may be provided with fixed high and low pressure values in the pressure sensors 42 and 48, and the pump 40 in FIG. 2 or the double-head blood pump 40-54 in FIG. 3 may be fixed to deliver a fixed amount of blood per unit time to the fluid treatment device 12. However, for the same reasons as indicated in relation to FIG. 1, the speed of the pump 40 in FIG. 2 and the double-head blood pump 40-54 in FIG. 3 are most preferably variable speed pumps which are manually adjustable.

By virtue of the self-regulating nature of the apparatuses of the invention, stroke volumes for each selected pump speed is automatically maximized. No needs arise to count cycles or calculate stroke volumes. The flow rate can for example be read directly from a pump speed control knob for controlling the speed of pump 40. The two extremes would be firstly where essentially unlimited flow of fluid is available from the patient, e.g. as with a large catheter placed in a large central vein, and secondly where flow of fluid is limited, e.g. as with a small fistula.

Referring specifically to FIG. 2, it will be readily recognised that the pressure regulation leads to pump 54 automatically adjusting to follow the speed of pump 40 so that the pressure value set in pressure sensor 62 is maintained.

Regarding safety of operation, it will be recognised from above that any changes in resistance to flow will be automatically responded to by changes in the time taken for the clamp assembly 20 to switch from one extreme position to the other. This self-regulation aspect is of exceptional value since it enables dispensing with a variety of monitoring functions. This novel aspect also allows for simple alarm condition control. If said time period is too long, e.g. longer than 5 seconds, an alarm condition could be initiated, e.g. by means of a timer or time delay (not shown) adapted to stop the pump or pumps if pressure remains below the low limit pressure value in the arterial line chamber 10 for a period exceeding said time period of 5 seconds or if pressure remains above the high limit pressure value in the venous line reservoir 32 for a period exceeding said time period. A low pressure value in the arterial line reservoir 10 over said time period would indicate either that the blood pump 40 has been set at too high a speed for the amount of fluid passing to the arterial line reservoir 10 from the fluid source or that the single lumen catheter is obstructed. Similarly, a high pressure value in the venous line reservoir 32 over said time period would indicate obstruction. A most preferable additional alarm condition in which pumps are stopped is when a low pressure value of about atmospheric pressure arises in the venous line reservoir 32, which would indicate that the venous line 30 is disconnected or that the single lumen catheter is not in place. An additional optional alarm condition in which pumps are stopped is a high pressure in the arterial line reservoir 10, again of about atmospheric pressure, indicating that the arterial line 14 is disconnected or that the catheter is not in place.

The apparatuses of the invention, as illustrated in the drawings, are particularly intended to achieve a simple user interface. Thus, in the constructions of FIGS. 1 and 2 for example, in which pressure values are fixed in pressure sensors 42 and 48, (and also in pressure sensor 62 for a particular fluid treatment device 12), the user will only be required to set pump 40 in motion after properly mounting of the fluid lines and fluid treatment device 12. The opening and closing of arterial and venous lines will set in automatically and in FIG. 2, the speed of the pump 54 will automatically follow the speed of pump 40 to maintain the pressure value set in pressure sensor 62.

I claim:

1. Apparatus including means for controlling the closing of an arterial line with substantially simultaneous opening of a venous line and means for the closing of said venous line with substantially simultaneous opening of said arterial line in a single lumen catheter assembly in which one end of the arterial line is connected to one arm of a Y-piece of the single lumen catheter and the other end of the arterial line is connected to an inlet end of a fluid treatment device, and in which one end of the venous line is connected to an outlet end of a fluid treatment device and the other end of the venous line is connected to the second arm of the Y-piece of the single lumen catheter, so that untreated fluid withdrawn from a fluid source through said single lumen catheter and said arterial line will pass through a fluid source through said venous line and single lumen catheter, and which further comprises:

an arterial line reservoir which is connected into the arterial line between the Y-piece of the single lumen catheter and the fluid treatment device;

a venous line reservoir which is connected into the venous line between the fluid treatment device and the Y-piece of the single lumen catheter;

a first pump operable between the arterial line reservoir and the fluid treatment device;

a second pump operable between the fluid treatment device and the venous line reservoir, the first pump being a constant speed pump and the second pump being a variable speed pump variable in response to pressure fluctuations in fluid between the two pumps;

high limit sensor means connected to the venous line reservoir for sensing a higher limit quantity of treated fluid available in the venous line reservoir;

arterial line closing means, upstream from said arterial line reservoir, for closing the arterial line which is activatable to close the arterial line in response to a first signal transmitted to the arterial line closing means by the high limit sensor means;

low limit sensor means connected to the arterial line reservoir for sensing a low limit quantity of untreated fluid available in the arterial line reservoir; and venous line closing means, downstream from said venous line reservoir, for closing the venous line in response to a second signal transmitted to the venous line closing means by the low limit sensor;

the arterial line closing means and the venous line closing means being interconnected so that when the arterial line closing means is activated by said first signal to close the arterial line, the venous line closing means is substantially simultaneously deactivated to open the venous line and so that when the venous line closing means is activated by said second signal to close the venous line, the arterial line closing means is substantially simultaneously deactivated to open the arterial line.

2. Apparatus according to claim 1, in which the constant speed pump is provided with means for manually adjusting said constant speed.

3. Apparatus according to claim 1, wherein said means for controlling the closing of an arterial line with substantially simultaneous opening of said venous line and said means for controlling the closing of a venous line with substantially simultaneous opening of said arterial line collectively comprise a closing member including:

a laterally displaceable member positioned between said venous line and said arterial line, said laterally displaceable member being laterally displaceable toward said arterial line and toward said venous line in response to said first signal and said second signal, respectively;

a first essentially stationary abutment element coplanar with and opposite said laterally displaceable member positioned just outside said arterial line;

a second essentially stationary abutment element coplanar with and opposite said displaceable member positioned just outside said venous line;

whereby, when said displaceable member is fully laterally displaced toward said arterial line, said arterial line is pinched between said laterally displaceable member and said first abutment element and is thereby essentially fully closed while said venous line is substantially simultaneously essentially fully opened, and when said laterally displaceable member is fully laterally displaced toward said venous line, said venous line is pinched between said laterally displaceable member and said second abutment element and is thereby essentially fully closed while said arterial line is substantially simultaneously essentially fully opened.

4. Apparatus according to claim 1, in which there is provided a pressure sensor for sensing pressure fluctuations in fluid between the two pumps, and means for varying the variable speed pump in response to a signal transmitted by the pressure sensor to said variable speed pump.

5. Apparatus according to claim 4, in which the pressure sensor includes a pressure reservoir provided downstream of the fluid treatment device and upstream of the second pump.

6. Apparatus according to claim 5, in which the pressure reservoir includes means for connection to an infusion line for introducing a substitution fluid for substituting fluid removed from fluid treated by the fluid treatment device.

7. Apparatus according to claim 1, in which the high limit sensor means is adapted to transmit said first signal to the arterial line closing means when a preselected fixed high pressure value develops in the venous line reservoir.

8. Apparatus according to claim 1, in which the low limit sensor means is adapted to transmit said second signal to the venous line closing means when a preselected fixed low pressure value develops in the arterial line reservoir.

* * * * *